United States Patent
Kafka et al.

(10) Patent No.: US 6,822,978 B2
(45) Date of Patent: Nov. 23, 2004

(54) REMOTE UV LASER SYSTEM AND METHODS OF USE

(75) Inventors: James D. Kafka, Palo Alto, CA (US); David E. Spence, Mountain View, CA (US)

(73) Assignee: Spectra Physics, Inc., Mountain View, CA (US)

(*) Notice: Subject to any disclaimer, the term of this patent is extended or adjusted under 35 U.S.C. 154(b) by 306 days.

(21) Appl. No.: 10/194,439

(22) Filed: Jul. 12, 2002

(65) Prior Publication Data

US 2003/0008448 A1 Jan. 9, 2003

Related U.S. Application Data

(63) Continuation-in-part of application No. 10/114,337, filed on Apr. 1, 2002, now Pat. No. 6,734,387, which is a continuation-in-part of application No. 09/321,499, filed on May 27, 1999, now Pat. No. 6,373,565.

(51) Int. Cl.[7] .................... H01S 3/098; H01S 3/10; H01S 3/08; G02B 6/26
(52) U.S. Cl. ................ 372/18; 372/19; 372/21; 372/22; 372/108; 385/31; 359/326
(58) Field of Search .............................. 372/11, 19, 21, 372/22, 75, 99, 108; 385/31–37, 147; 359/326–332

(56) References Cited

U.S. PATENT DOCUMENTS

| | | |
|---|---|---|
| 3,626,143 A | 12/1971 | Fry |
| 4,377,340 A | 3/1983 | Green et al. ............ 356/237 |
| 4,630,276 A | 12/1986 | Moran .................... 372/15 |
| 4,933,944 A | 6/1990 | McGraw |
| 4,942,582 A | 7/1990 | Kintz et al. ............. 372/18 |
| 4,989,984 A | 2/1991 | Salinger ................. 356/445 |
| 5,127,726 A | 7/1992 | Moran .................... 356/237 |
| 5,170,063 A | 12/1992 | Miyazaki et al. ....... 250/572 |
| 5,177,559 A | 1/1993 | Batchelder ............. 356/237 |
| 5,361,275 A | 11/1994 | Opower |
| 5,394,413 A | 2/1995 | Zayhowski .............. 372/10 |
| 5,410,559 A | 4/1995 | Nighan, Jr. et al. |
| 5,623,341 A | 4/1997 | Hunt ..................... 356/300 |
| 5,627,854 A | 5/1997 | Knox ..................... 372/99 |
| 5,699,160 A | 12/1997 | Barenboim et al. |
| 5,712,701 A | 1/1998 | Clementi et al. ....... 356/237.1 |
| 5,812,308 A | 9/1998 | Kafka et al. ........... 359/346 |
| 5,834,160 A | 11/1998 | Ferry et al. ............ 430/313 |
| 5,909,306 A | 6/1999 | Goldberg et al. ....... 359/341 |
| 5,936,983 A | 8/1999 | Yusong et al. .......... 372/22 |
| 5,940,418 A | 8/1999 | Shields |
| 5,987,049 A | 11/1999 | Weingarten et al. |
| 6,061,370 A | 5/2000 | Yin ...................... 372/22 |
| 6,071,677 A | 6/2000 | Ishimatsu et al. |
| 6,113,835 A | 9/2000 | Kato et al. |
| 6,157,663 A | 12/2000 | Wu et al. ............... 372/75 |
| 6,185,235 B1 | 2/2001 | Cheng et al. ........... 372/39 |
| 6,188,704 B1 | 2/2001 | Kwon et al. |
| 6,246,706 B1 | 6/2001 | Kafka et al. ........... 372/24 |
| 6,421,573 B1 | 7/2002 | Kafka et al. ........... 700/121 |
| 2002/0003130 A1 | 1/2002 | Sun et al. |

FOREIGN PATENT DOCUMENTS

| | | | |
|---|---|---|---|
| DE | 195 29 656 A1 | 2/1997 | ............ G03F/7/20 |
| EP | 0 818 858 A2 | 1/1998 | ......... H01S/3/0941 |
| WO | WO 98/33096 | 7/1998 | ............ G03F/1/08 |

*Primary Examiner*—Don Wong
*Assistant Examiner*—Armando Rodriguez
(74) *Attorney, Agent, or Firm*—Paul Davis; Heller Ehrman White & McAuliffe

(57) ABSTRACT

A laser apparatus includes a modelocked laser system with a high reflector and an output coupler that define an oscillator cavity. An output beam is produced from the oscillator cavity. A gain medium and a modelocking device are positioned in the oscillator cavity. A diode pump source produces a pump beam that is incident on the gain medium. A second harmonic generator is coupled to the oscillator cavity. A third harmonic generator that produces a UV output beam, is coupled to the second harmonic generator. A photonic crystal fiber is provided with a proximal end coupled to the laser system. A delivery device is coupled to a distal portion of the photonic crystal fiber.

58 Claims, 5 Drawing Sheets

REMOTE UV LASER SYSTEM AND METHODS OF USE

CROSS REFERENCE TO RELATED APPLICATIONS

This application is a continuation-in-part of Ser. No. 10/114,337, filed Apr. 1, 2002, now U.S. Pat. No. 6,734,387, which is a continuation in part of Ser. No. 09/321,499, filed May 27, 1999, now U.S. Pat. No. 6,373,565, issued Apr. 16, 2002.

BACKGROUND

1. Field of the Invention

This invention relates generally to UV and visible laser systems, and their methods of use, and more particularly to UV and visible laser systems that are suitable for semiconductor inspection or processing.

2. Description of Related Art

An increasing number of laser applications in the semiconductor industry require UV or visible laser light. These applications include inspection as well as materials processing tasks. Many of these applications require that the sample under test be kept clean or be in close proximity to processing equipment, and thus the entire machine is located in a clean room environment.

Diode-pumped solid-state lasers are finding increasing acceptance in this market because of their robustness. These systems consist of several subsystems: a power supply to run the pump diodes, the pump diodes themselves, the laser head, and a harmonic conversion device to generate the visible or UV radiation. Typically, the entire laser system is included within the semiconductor-processing machine, which is located in the clean room.

Diodes used as the pump source can be positioned in the power supply. Pump light is then coupled from the diodes in a multi-mode fiber, and is conveyed to the laser head by an armored fiber cable. In this way, the power supply and diodes can be located remotely, while the laser head and harmonic conversion device are located in the semiconductor-processing machine. The power supply and diodes can be outside the machine or even outside the clean room.

However, positioning the diodes in the power supply, followed by coupling the diode pump light in a multimode fiber, works because the pump light is: in the IR, continuous wave, and not diffraction limited. In contrast, the output of the laser is visible or UV, is often pulsed, and has a diffraction limited beam. Thus, single mode fibers are required to preserve the beam quality, but are problematic with both pulses and UV radiation.

There is a need for improved UV and visible laser systems that are suitable for semiconductor inspection or processing. There is a further need for UV and visible laser systems for semiconductor inspection or processing applications where the laser resonator and power supply are positioned at a location external to a clean room.

SUMMARY OF THE INVENTION

Accordingly, an object of the present invention is to provide diode-pumped lasers, and their methods of use, in remote location applications.

Another object of the present invention is to provide diode-pumped lasers, and their methods of use, in semiconductor inspection or processing applications with the laser resonator and power supply positioned at a location external to a clean room.

These and other objects of the present invention are achieved in a laser apparatus that includes a modelocked laser system with a high reflector and an output coupler that define an oscillator cavity. An output beam is produced from the oscillator cavity. A gain medium and a modelocking device are positioned in the oscillator cavity. A diode pump source produces a pump beam that is incident on the gain medium. A second harmonic generator is coupled to the oscillator cavity. A third harmonic generator that produces a UV output beam, is coupled to the second harmonic generator. A photonic crystal fiber is provided with a proximal end coupled to the laser system. A delivery device is coupled to a distal portion of the photonic crystal fiber.

In another embodiment of the present invention, a laser apparatus includes a modelocked laser system with a high reflector and an output coupler that define an oscillator cavity and produces an output beam. A gain medium and a modelocking device are positioned in the oscillator cavity. A diode pump source produces a pump beam that is incident on the gain medium. A first amplifier is also included. A second harmonic generator is coupled to the first amplifier. A third harmonic generator that produces a UV output beam, is coupled to the second harmonic generator. A photonic crystal fiber is provided with a proximal end coupled to the laser system. A delivery device is coupled to a distal portion of the photonic crystal fiber.

In another embodiment of the present invention, a laser apparatus includes a modelocked IR laser system with a high reflector and an output coupler that define an oscillator cavity. A gain medium and a modelocking device are positioned in the oscillator cavity. A diode pump source produces a pump beam that is incident on the gain medium. A photonic crystal fiber is provided with a proximal end coupled to the IR laser system. A harmonic conversion delivery device is coupled to a distal end of the photonic crystal fiber.

In another embodiment of the present invention, a laser apparatus includes a modelocked IR laser system with a high reflector and an output coupler that define an oscillator cavity. A gain medium and a modelocking device are positioned in the oscillator cavity. A diode pump source produces a pump beam incident on the gain medium. A first amplifier is also included. A photonic crystal fiber has a proximal end coupled to the IR laser system. A harmonic conversion delivery device is coupled to a distal end of the photonic crystal fiber.

In another embodiment of the present invention, a method of delivering a UV output beam to a remote location provides a modelocked infrared laser system. The laser system includes a high reflector and an output coupler that define an oscillator cavity that produces an output beam. A gain medium and a modelocking device are positioned in the oscillator cavity. A photonic crystal fiber is provided and has a proximal portion coupled to the laser system, and a distal portion coupled to a delivery device. The infrared laser system is positioned at a distance from the remote location. A UV output beam is produced at a distance from the remote location. The UV output beam is delivered to the delivery device at the remote location.

In another embodiment of the present invention, a method of delivering an UV output beam to a remote location is provided. A modelocked IR laser system includes a high reflector and an output coupler that define an oscillator cavity that produces an output beam. A gain medium and a modelocking device are positioned in the oscillator cavity. A diode pump source produces a pump beam that is incident on the gain medium. A harmonic conversion delivery device is positioned at the remote location. A photonic crystal fiber is provided that has a proximal portion coupled to the IR laser system, and a distal portion coupled to the harmonic conversion delivery device. The IR laser beam is delivered with the photonic crystal fiber from the IR laser system to the harmonic conversion delivery device. A UV beam is produced from the harmonic conversion delivery device at the remote location.

DETAILED DESCRIPTION

Figure 1:
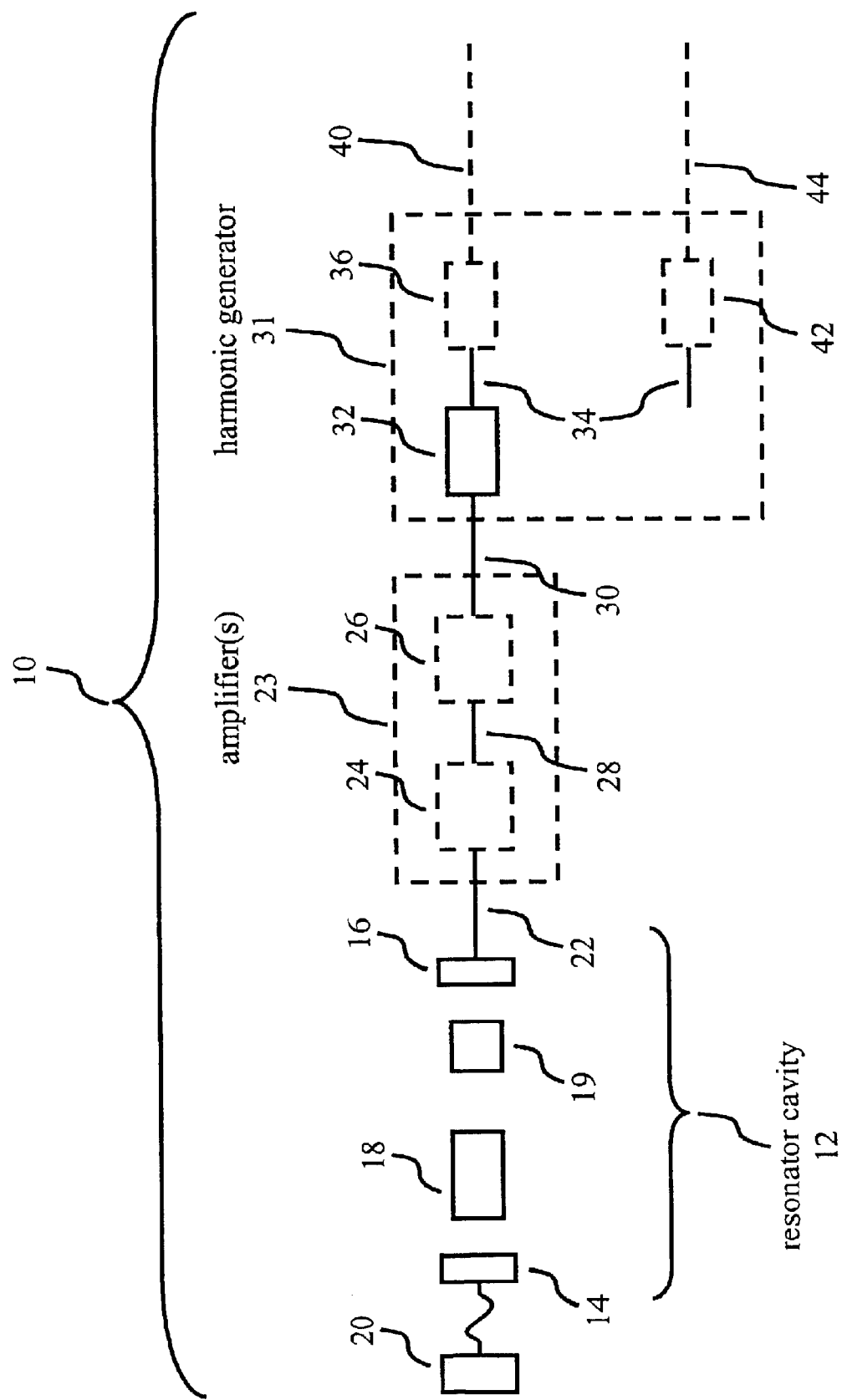
FIG. 1 is a block diagram that illustrates one embodiment of a laser or laser/amplifier system that produces UV light utilized with the systems and methods of the present invention.

In various embodiments, the present invention provides a laser apparatus that has a laser system, and its methods of use. In one embodiment, the laser system includes an oscillator system or an oscillator/amplifier system. The oscillator/amplifier system is similar to the oscillator system but includes one or more amplifiers. The oscillator and oscillator/amplifier systems can be coupled with second, third, fourth, and fifth harmonic generators. A second harmonic generator can be used alone with the oscillator and oscillator/amplifier systems and in various combinations with third, fourth and fifth harmonic generators. Additionally, the harmonic generators can be coupled with an OPO. The OPO can be pumped by a fundamental beam from an oscillator or from the harmonic generators. An output of the OPO can be mixed with the harmonic generators to generate an additional variable wavelength source.

In one embodiment, the oscillator system includes an Nd:YVO$_4$ gain medium and is modelocked by a multiple quantum well absorber. In a specific embodiment of this oscillator system, the oscillator is pumped by a single fiber-coupled diode bar that provides 13 watts of pump power incident on the Nd:YVO$_4$ gain medium, and typically produces 5–6 watts of 5–15 picosecond pulses at 80 MHz repetition rate. In another embodiment, an oscillator/amplifier system includes an Nd:YVO$_4$ gain medium modelocked by a multiple quantum well absorber, a double pass amplifier and two single pass amplifiers. Each of the amplifiers has an Nd:YVO$_4$ gain medium and is pumped by two fiber-coupled diode pump sources. This oscillator/amplifier system produces 25–30 watts of 5–15 picosecond pulses at 80 MHz repetition rate. In another embodiment, a pumping wavelength of 880 nm is used for increased power with a similar value of the thermal lens in the gain medium.

The oscillator and oscillator/amplifier systems can be modelocked with a multiple quantum well saturable absorber, a non-linear mirror modelocking method, a polarization coupled modelocking method, or other modelocking techniques, including but not limited to use of an AO modulator. An example of a quantum well saturable absorber is disclosed in U.S. Pat. No. 5,627,854, incorporated herein by reference. An example of a non-linear mirror modelocking method is disclosed in U.S. Pat. No. 4,914,658, incorporated herein by reference. An example of a polarization coupled modelocking method is disclosed U.S. Pat. No. 6,021,140, incorporated herein by reference. In order to produce shorter pulses and a single output beam the gain media is positioned adjacent to a fold mirror as described in U.S. Pat. No. 5,812,308, incorporated herein by reference.

A high power oscillator system with the performance of an oscillator/amplifier system is achieved by using multiple fiber-coupled diodes and either a non-linear mirror modelocking technique or a polarization coupled modelocking method. This high power oscillator system produces 10–20 watts of output power with 4–10 picosecond pulses at a repetition rate of 80–120 MHz.

High repetition rates are desirable for applications where the laser system is used as a quasi-CW source. For some applications, 80 MHz repetition rate is sufficiency high to be considered quasi-CW. This repetition rate is achieved with an oscillator cavity length of 1.8 meters. When the cavity length is shortened to 0.4 meters the repetition rate increases to 350 MHz.

Referring now to FIG. 1, one embodiment of an oscillator system 10 has a resonator cavity 12 defined by a high reflector 14 and an output coupler 16. A gain media 18 is positioned in resonator cavity 12. Suitable gain media 18 include but are not limited to, Nd:YVO$_4$, Nd:YAG, Nd:YLF, Nd:Glass, Ti:sapphire, Cr:YAG, Cr:Forsterite, Yb:YAG, Yb:glass, Yb:KGW, Yb:KYW, KYbW, YbAG, and the like. A preferred gain media 18 is Nd:YVO$_4$. A modelocking device 19 is positioned in oscillator cavity 12. In one embodiment, oscillator system 10 is modelocked and pumped by a fiber-coupled bar 20 that produces 13 watts of power. Oscillator cavity 12 can produce 1 to 6 watts of power nominally at an 80 MHz repetition rate with pulse widths of 5 to 15 picoseconds.

Optionally included are one or more amplifiers, generally denoted as 23. An output beam 22 from resonator cavity 12 can be amplified by a first amplifier 24. A second amplifier 26 can be included. Additional amplifiers may also be included to increase power. Typically, amplifiers 24 and 26 have the same gain media used in resonator cavity 12. Nd:YVO$_4$ is a suitable gain media material because it provides high gain in an amplifier. The high gain of Nd:YVO$_4$ provides a simplified amplifier design requiring fewer passes through the gain media. Amplifiers 24 and 26 produce output beams 28 and 30 respectively. Amplifiers 24 and 26 can be single pass, double pass and four pass. A four pass amplifier is disclosed in U.S. Pat. No. 5,812,308, incorporated herein by reference. Oscillator/amplifier system 10 using an oscillator, a double pass amplifier and two single pass amplifiers can provide 30 watts of average power.

Output beams 22, 28 or 30 can be incident on a harmonic generator generally denoted as 31 and can include a second harmonic generator 32. An output 34 from second harmonic generator 32 can be incident on a third harmonic generator 36 to produce an output beam 40. Alternatively, output 34 can be incident on a fourth harmonic generator 42 to produce an output beam 44. It will be appreciated that oscillator system 10 can include various combinations of harmonic generators 32, 36, 42 as well as a fifth or higher harmonic generators or an OPO. Second harmonic generator 32 can use non-critically phase matched LBO, third harmonic generator 36 can employ type II LBO and fourth harmonic generator 42 can use type I BBO.

In a specific embodiment, oscillator system 10 includes oscillator cavity 12 with harmonic generation. Output beam 22 is incident on second harmonic generator 32. In this specific embodiment, oscillator system 10 may also include third or fourth harmonic generators 36 and 42. The output power of this oscillator system 10 is 5 watts at 1064 nm. A harmonic generation system produces 2 watts at 532 nm or 1 watt at 355 nm or 200 milliwatts at 266 nm.

In another specific embodiment, $Nd:YVO_4$ is the gain media of oscillator/amplifier system 10, and 29 watts of 7 picosecond pulses at 1064 nm is produced. The harmonic generation system can generate 22 watts at 532 nm or 11 watts at 355 nm or 4.7 watts at 266 nm.

In another specific embodiment, oscillator/amplifier system 10 includes oscillator cavity 12, a four-pass amplifier 24 and second harmonic generator 32 to produce 2 watts at 532 nm. This oscillator/amplifier system can pump an OPO that utilizes non-critically phase matched LBO as described in Kafka, et al., J. Opt. Soc. Am. B 12, 2147–2157 (1995) incorporated herein by reference.

In another specific embodiment, oscillator/amplifier system 10 includes oscillator cavity 12, a double pass amplifier 24 and three single pass amplifiers 26 that produces 42 watts of 7 picosecond pulses at 1064 nm. This oscillator/amplifier system can pump an OPO using non-critically phase-matched KTA and produce an output beam at 1535 nm. The output beam at 1535 nm can be mixed with a 1064 nm beam to provide 11.6 watts at 629 nm, as described in Nebel, et al., in *Conference on Lasers and Electro-Optics*, Vol. 6 of 1998 OSA Technical Digest Series (Optical Society of America, Washington, D.C., 1998) postdeadline paper CPD3. Fiber-coupled bars that produce 40 Watts, commercially available from Spectra Physics Semiconductor Lasers, Tucson, Ariz. can be used to increase the output power of oscillator or oscillator/amplifier systems 10.

The use of a $Nd:YVO_4$ gain media 18 with a doping level of less than 0.5% can also be used to increase the output power of oscillator or oscillator/amplifier systems 10. The combination of the 40 watt fiber-coupled bars with the low doped $Nd:YVO_4$ gain media greatly increases the output power of oscillator and oscillator/amplifier systems 10. Use of low doped $Nd:YVO_4$ gain media 18 can also reduce the sensitivity of oscillator cavity 12 to misaligmnent as well as improve the output beam quality from an amplifier 24 or 26. The use of low doped $Nd:YVO_4$ gain media, a longer $Nd:YVO_4$ gain media as well as a larger pump volume in $Nd:YVO_4$ gain media is disclosed in U.S. Pat. No. 6,185,235, incorporated herein by reference. Oscillator system and/or oscillator/amplifier system 10, are collectively designated as laser system 110, and output beams 22, 28, 30, 34, 40 or 44 are collectively denoted as output beam 112.

Figure 2:
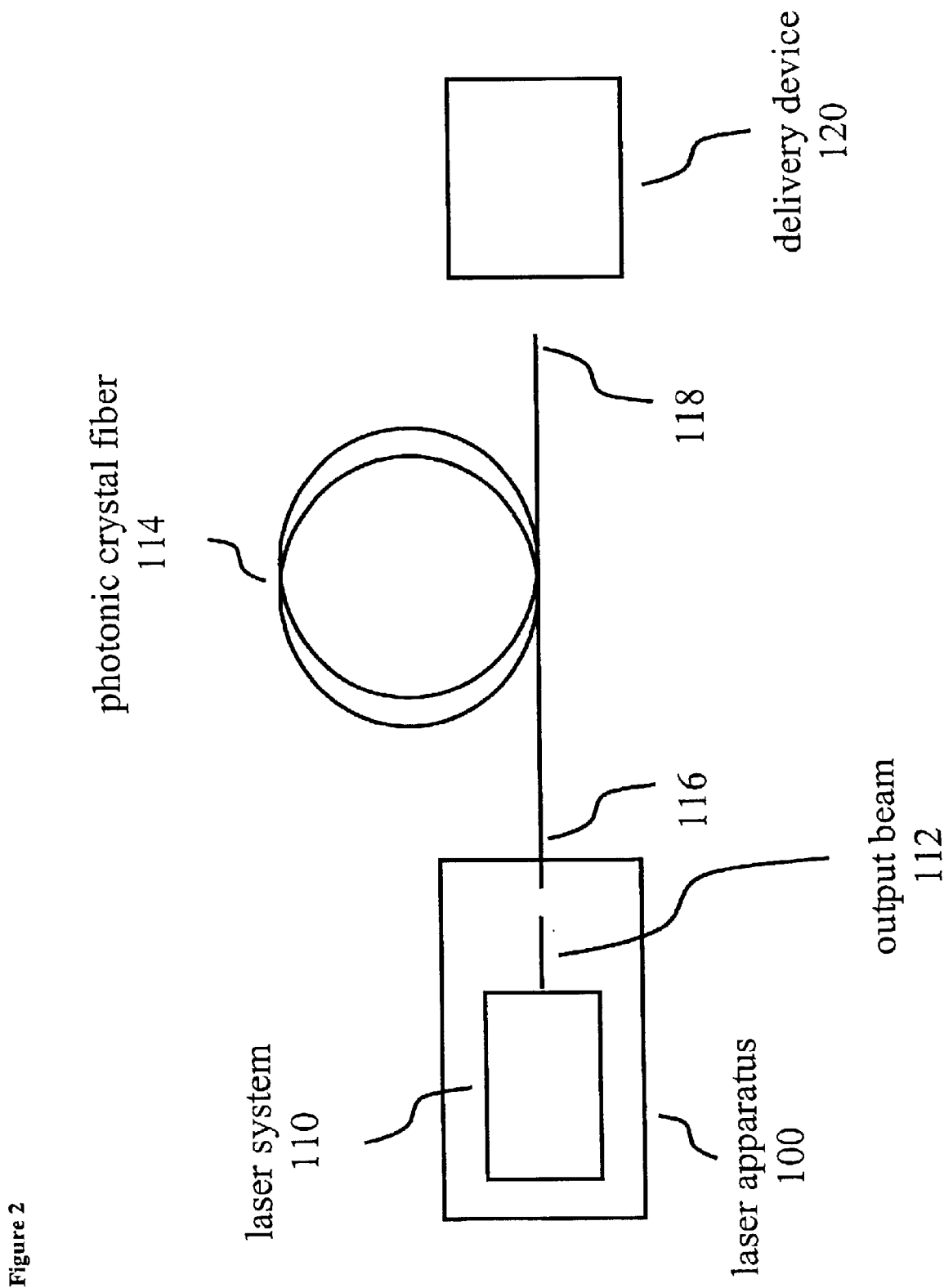
FIG. 2 is a block diagram of one embodiment of a system of the present invention illustrating the combination of the system of FIG. 1, a photonic crystal fiber and a delivery device.

Referring now to FIG. 2, one embodiment of the present invention is a laser apparatus 100 that includes laser system 110. A photonic crystal fiber 114 has a proximal portion 116 coupled to laser system 110 and a distal portion 118 coupled to a delivery device 120. Suitable delivery devices include, but are not limited to, one or more lenses, mirrors, scanners, microscopes, telescopes, acousto-optic or electro-optic devices, and the like.

A characteristic of photonic crystal fiber 114 is that is has low absorption at the wavelength of interest. Additionally, the damage threshold and threshold for nonlinear effects are both high. By way of illustration, and without limitation, the threshold for nonlinear effects can be substantially greater than 1 kilowatt. In one embodiment, photonic crystal fiber 114 is a hollow core single mode photonic crystal fiber. Hollow core single mode photonic crystal fiber 114 guides output beam 112 in air and preserves its mode quality. These fibers are commercially available from Blaze Photonics, Bath, England.

Figure 3:
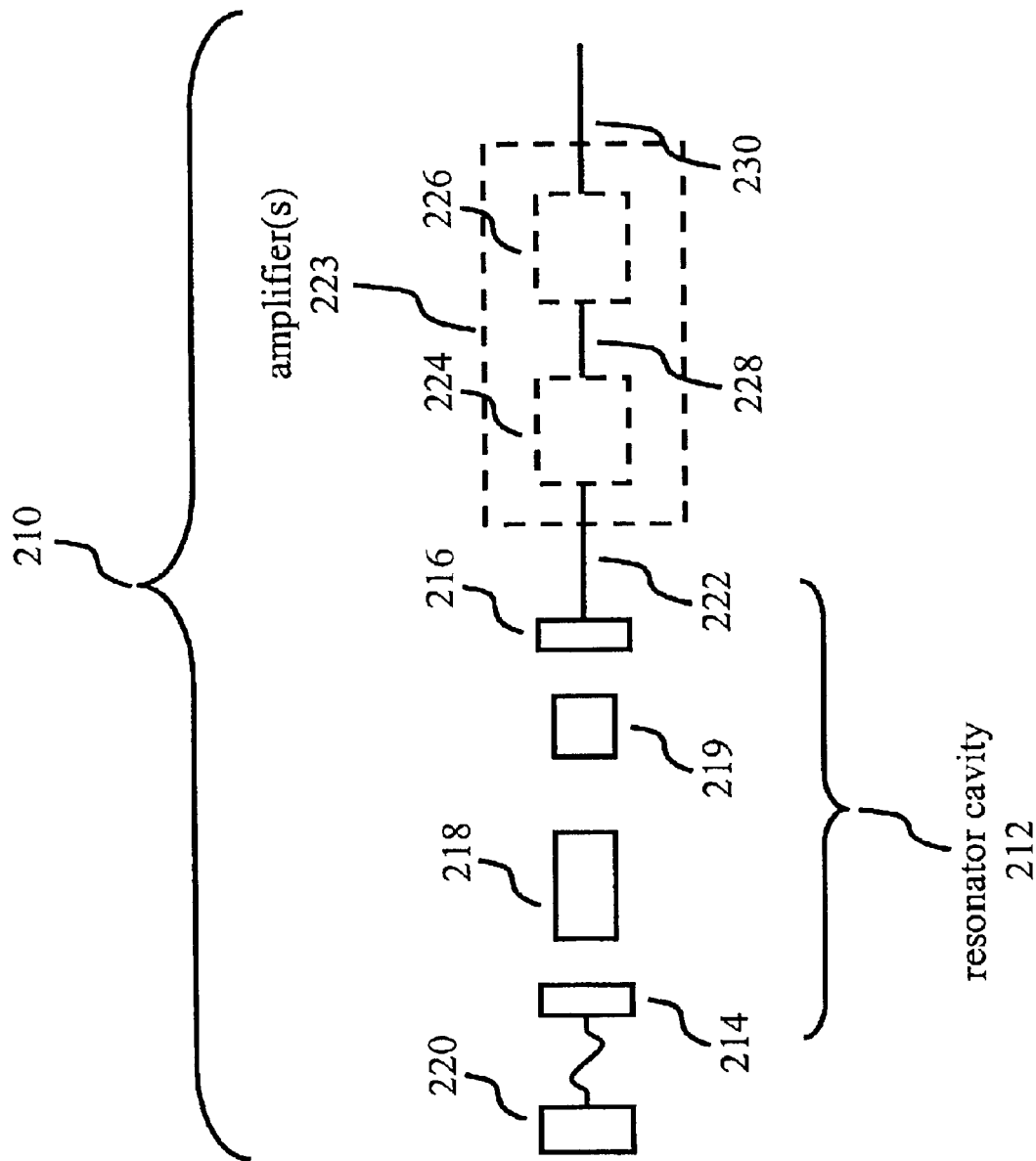
FIG. 3 is a block diagram that illustrates another embodiment of a laser or laser/amplifier system that produces IR light utilized with the systems and methods of the present invention.

As illustrated in FIG. 3, in another embodiment, laser system 210 is an IR laser system that produces an output of a wavelength between 1000 nm and 1100 and most preferably 1064 nm. The power range can be between 5 to 30 W.

IR laser system 210 is similar to laser system 10 but does not include the harmonic generators. IR laser system 210 has a resonator cavity 212, high reflector 214, output coupler 216, a gain media 218 and a modelocking device 219. IR laser system 210 is pumped by a pump source 220 and produces an output beam 222. IR laser system 210 can include one or more amplifiers, 223 that amplify output beam 222. Amplifier 223 can include a first amplifier 224, a second amplifier 226 and additional amplifiers depending on the application.

Figure 4:
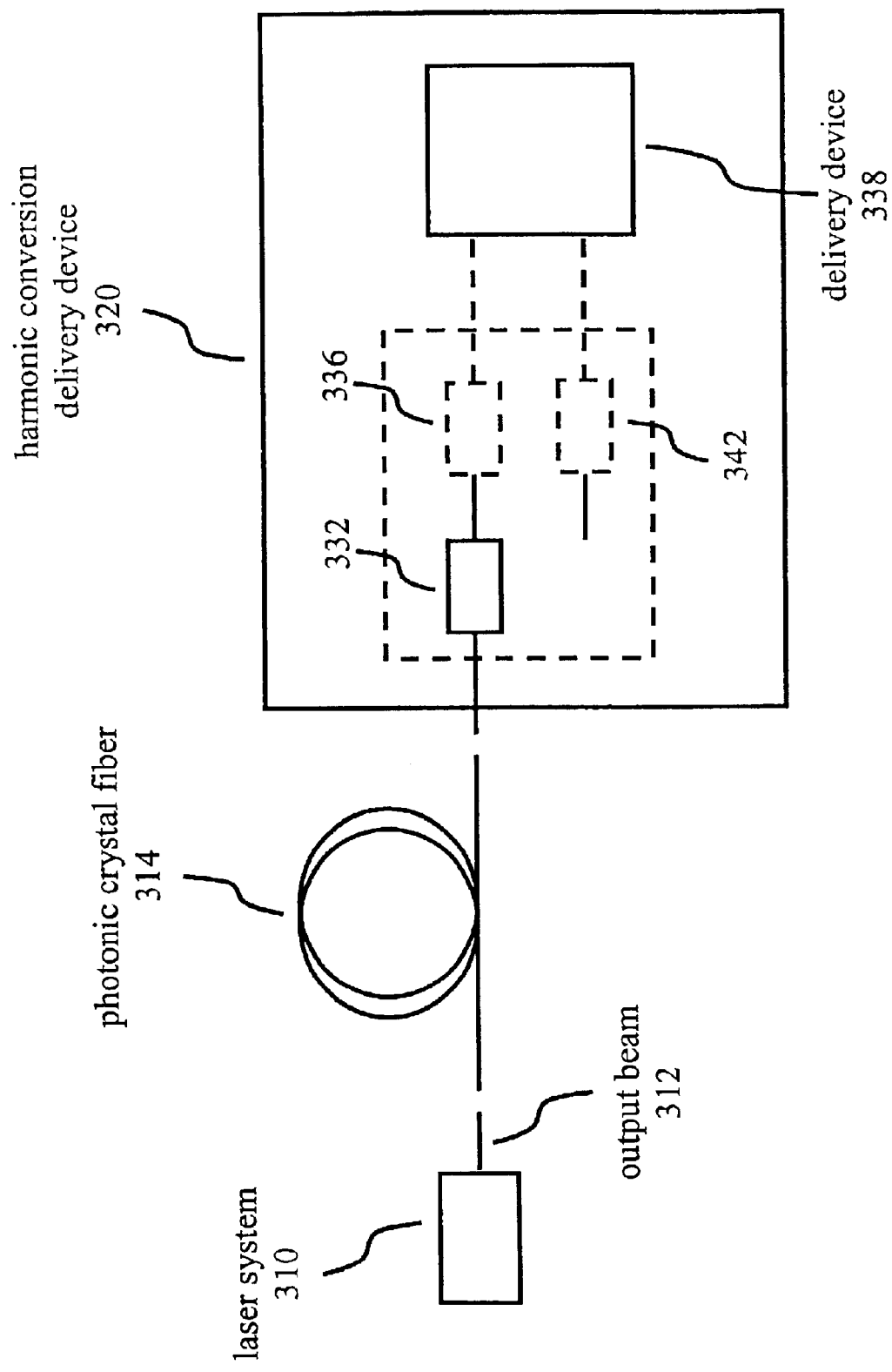
FIG. 4 is a block diagram of one embodiment of a system of the present invention illustrating the combination of the system of FIG. 3, a photonic crystal fiber and a harmonic conversion delivery device.

Referring to FIG. 4, IR laser system 310 is similar to IR laser system 210, and produces an output beam 312. Output beam 312 is coupled to a photonic crystal fiber 314, which in turn is coupled to a harmonic conversion delivery device 320. Harmonic conversion delivery device 320 can include various combinations of harmonic generators 332, 336, 342, as well as fifth or higher harmonic generators or an OPO, and a delivery device 338 which is substantially the same as delivery device 120.

Figure 5:
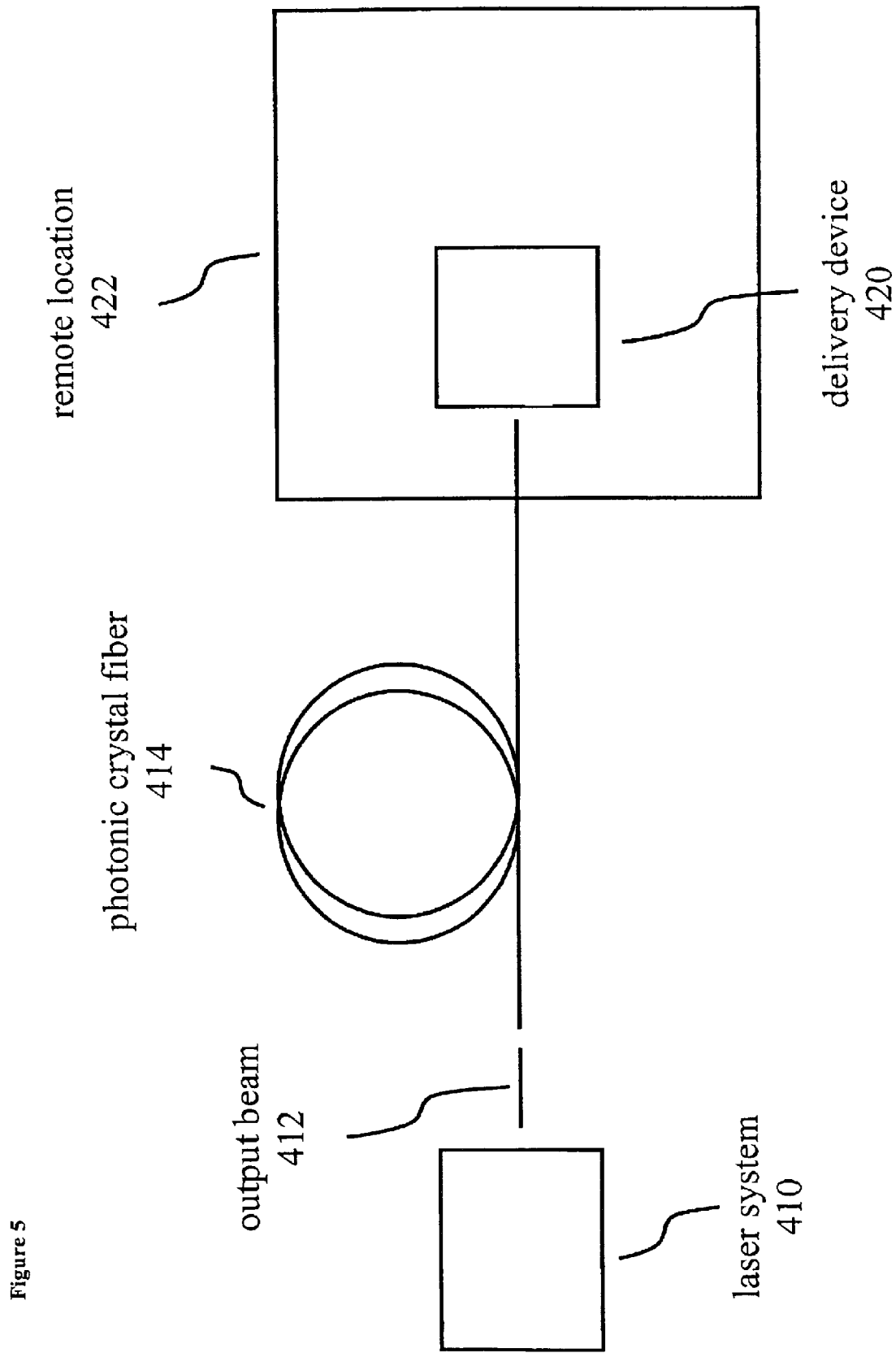
FIG. 5 illustrates one embodiment of the present invention utilizing the systems of FIG. 2 or FIG. 4 in a remote location.

In one method of the present invention, laser systems 110 or 310, collectively 410, are positioned remotely from a remote location 422. Delivery device 120 or harmonic conversion delivery device 320, collectively 420, is positioned at remote location 422. Output beams 112 or 312, collectively 412, from laser 410, is delivered by photonic crystal fiber 414 to delivery device 420 at a remote location 422 as shown in FIG. 5. In the embodiment of IR laser 310, its power supply, pump diodes, and IR laser head are all positioned away from remote location 422. Examples of remote location 422 include clean rooms, vacuum enclosures, enclosed machinery and the like.

In one embodiment, remote location 422 is a clean room that is utilized in the semiconductor industry. However, it will be appreciated that the present invention also finds utility in a wide variety of different types of clean rooms, and other remote locations, where it is desired to position laser system 410 apart from remote location 422.

In one embodiment, laser system 410 is positioned from 2 to 200 meters from remote location 422. In another embodiment, laser system 410 is positioned no more than 10 meters from remote location 422.

Laser system 410 is positioned away from remote location 422 and the heat produced by laser system 410 is not introduced to remote location 422. By positioning laser system 410 away from remote location 422, maintenance of laser system 410 can be carried out without disrupting remote location 422 as well as items located there.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A laser apparatus, comprising:
    a modelocked UV laser system including a high reflector and an output coupler defining an oscillator cavity, a gain medium and a modelocking device positioned in the oscillator cavity, a diode pump source producing a pump beam incident on the gain medium, a second harmonic generator coupled to the oscillator cavity and to a third harmonic generator, the modelocked laser system producing a UV output beam;
    a photonic crystal fiber with a proximal end coupled to the UV laser system; and
    a delivery device coupled to a distal portion of the photonic crystal fiber.

2. The apparatus of claim 1, wherein the photonic crystal fiber is configured to deliver a good mode focusable to within 1.5 times the diffraction limit and a majority of power of the UV output beam.

3. The apparatus of claim 1, wherein the photonic crystal fiber is a hollow core photonic crystal fiber.

4. The apparatus of claim 1, wherein the gain medium is $Nd:YVO_4$, Nd:YAG, Nd:YLF, Nd:Glass, Ti:sapphire, Cr:YAG, Cr:Forsterite, Yb:YAG, Yb:KGW, Yb:KYW, Yb:glass, KYbW and YbAG.

5. The apparatus of claim 1, wherein the gain medium is $Nd:YVO_4$.

6. The apparatus of claim 5, wherein the $Nd:YVO_4$ gain medium has a doping level of less than 0.5%.

7. The apparatus of claim 5, wherein the diode pump source has an output wavelength of 880 nm.

8. The apparatus of claim 1, wherein the diode pump source is fiber coupled.

9. The apparatus of claim 1, wherein the modelocking device is a multiple quantum well saturable absorber.

10. The apparatus of claim 1, wherein the modelocking device is a non-linear mirror modelocker.

11. The apparatus of claim 1, wherein the modelocking device is a polarization-coupled modelocker.

12. The apparatus of claim 1, wherein the modelocking device is an acousto-optic modulator.

13. The apparatus of claim 1, wherein the second harmonic generator is made of LBO.

14. The apparatus of claim 1, wherein the third harmonic generator is made of type II LBO.

15. The apparatus of claim 1, wherein the third harmonic generator is replaced by a fourth harmonic generator.

16. The apparatus of claim 15, wherein the fourth harmonic generator is made of type I BBO.

17. A laser apparatus, comprising:
    a modelocked UV laser system including a high reflector and an output coupler defining an oscillator cavity, a gain medium and a modelocking device positioned in the oscillator cavity, a diode pump source producing a pump beam incident on the gain medium, at least one amplifier, a second harmonic generator coupled to the at least one amplifier and to a third harmonic generator, the UV laser system producing a UV output beam;
    a photonic crystal fiber with a proximal end coupled to the UV laser system; and
    a delivery device coupled to a distal portion of the photonic crystal fiber.

18. The apparatus of claim 17, wherein the photonic crystal fiber is configured to deliver a good mode focusable to within 1.5 times the diffraction limit and a majority of power of the UV output beam.

19. The apparatus of claim 17, wherein the photonic crystal fiber is a hollow core photonic crystal fiber.

20. The apparatus of claim 17, wherein the gain medium is $Nd:YVO_4$, Nd:YAG, Nd:YLF, Nd:Glass, Ti:sapphire, Cr:YAG, Cr:Forsterite, Yb:YAG, Yb:KGW, Yb:KYW, Yb:glass, KYbW and YbAG.

21. The apparatus of claim 17, wherein the gain medium is $Nd:YVO_4$.

22. The apparatus of claim 21, wherein the $Nd:YVO_4$ gain medium has a doping level of less than 0.5%.

23. The apparatus of claim 21, wherein the diode pump source has an output wavelength of 880 nm.

24. A laser apparatus, comprising:
    a modelocked IR laser system including a high reflector and an output coupler defining an oscillator cavity, a gain medium and a modelocking device positioned in the oscillator cavity, and a diode pump source producing a pump beam incident on the gain medium;
    a photonic crystal fiber with a proximal end coupled to the IR laser system; and
    a harmonic conversion delivery device coupled to a distal end of the photonic crystal fiber.

25. The apparatus of claim 24, wherein the photonic crystal fiber is configured to deliver a good mode focusable to within 1.5 times the diffraction limit and a majority of power of the IR output beam.

26. The apparatus of claim 24, wherein the photonic crystal fiber is a hollow core photonic crystal fiber.

27. The apparatus of claim 24, wherein the gain medium is $Nd:YVO_4$, Nd:YAG, Nd:YLF, Nd:Glass, Ti:sapphire, Cr:YAG, Cr:Forsterite, Yb:YAG, Yb:KGW, Yb:KYW, Yb:glass, KYbW and YbAG.

28. The apparatus of claim 24, wherein the gain medium is $Nd:YVO_4$.

29. The apparatus of claim 28, wherein the $Nd:YVO_4$ gain medium has a doping level of less than 0.5%.

30. The apparatus of claim 28, wherein the diode pump source has an output wavelength of 880 nm.

31. A laser apparatus, comprising:
    a modelocked IR laser system including a high reflector and an output coupler defining an oscillator cavity, a gain medium and a modelocking device positioned in the oscillator cavity, and a diode pump source producing a pump beam incident on the gain medium, at least one amplifier;
    a photonic crystal fiber with a proximal end coupled to the IR laser system; and
    a harmonic conversion delivery device coupled to a distal end of the photonic crystal fiber.

32. The apparatus of claim 31, wherein the photonic crystal fiber is configured to deliver a good mode focusable to within 1.5 times the diffraction limit and a majority of power of the IR output beam.

33. The apparatus of claim 31, wherein the photonic crystal fiber is a hollow core photonic crystal fiber.

34. The apparatus of claim 31, wherein the gain medium is $Nd:YVO_4$, Nd:YAG, Nd:YLF, Nd:Glass, Ti:sapphire, Cr:YAG, Cr:Forsterite, Yb:YAG, Yb:KGW, Yb:KYW, Yb:glass, KYbW and YbAG.

35. The apparatus of claim 31, wherein the gain medium is $Nd:YVO_4$.

36. The apparatus of claim 35, wherein the $Nd:YVO_4$ gain medium has a doping level of less than 0.5%.

37. The apparatus of claim 35, wherein the diode pump source has an output wavelength of 880 nm.

38. A method of delivering a UV output beam to a remote location, comprising:

providing a modelocked UV laser system including a high reflector and an output coupler defining an oscillator cavity, a gain medium and a modelocking device each positioned in the oscillator cavity, a second harmonic generator and a third harmonic generator, the modelocked UV laser system producing a UV output beam;

providing a photonic crystal fiber with a proximal portion coupled to the UV laser system and a delivery device coupled to a distal portion of the photonic crystal fiber; and delivering a UV output beam from the laser system to the delivery device at the remote location.

39. The method of claim 38, wherein the remote location is a clean room.

40. The method of claim 39, wherein the laser system is positioned at an exterior of the clean room.

41. The method of claim 40, wherein the delivery device is positioned in an interior of the clean room.

42. The method of claim 38, wherein the photonic crystal fiber is configured to deliver a good mode focusable to within 1.5 times the diffraction limit and a majority of power of the UV output beam.

43. The method of claim 38, wherein the photonic crystal fiber is a hollow core photonic crystal fiber.

44. The method of claim 38, wherein the gain medium is Nd:YVO$_4$, Nd:YAG, Nd:YLF, Nd:Glass, Ti:sapphire, Cr:YAG, Cr:Forsterite, Yb:YAG, Yb:KGW, Yb:KYW, Yb:glass, KYbW and YbAG.

45. The method of claim 38, wherein the gain medium is Nd:YVO$_4$.

46. The method of claim 45, wherein the Nd:YVO$_4$ gain medium has a doping level of less than 0.5%.

47. The method of claim 38, wherein the diode pump source has an output wavelength of 880 nm.

48. A method of delivering an UV output beam to a remote location, comprising:

providing a modelocked IR laser system that includes a high reflector and an output coupler defining an oscillator cavity that produces an output beam, a gain medium and a modelocking device positioned in the oscillator cavity, and a diode pump source producing a pump beam incident on the gain medium;

providing a photonic crystal fiber with a proximal portion coupled to the IR laser system and a distal portion coupled to the harmonic conversion delivery device;

delivering the IR laser beam with the photonic crystal fiber from the IR laser system to a harmonic conversion delivery device; and producing a UV beam from the harmonic conversion delivery device at the remote location.

49. The method of claim 48, wherein the remote location is a clean room.

50. The method of claim 49, wherein the IR laser system is positioned at an exterior of the clean room.

51. The method of claim 50, wherein the harmonic conversion delivery device is positioned in an interior of the clean room.

52. The method of claim 48, wherein the photonic crystal fiber is configured to deliver a good mode focusable to within 1.5 times the diffraction limit and a majority of power of the UV output beam.

53. The method of claim 48, wherein the photonic crystal fiber is a hollow core photonic crystal fiber.

54. The method of claim 48, wherein the gain medium is Nd:YVO$_4$, Nd:YAG, Nd:YLF, Nd:Glass, Ti:sapphire, Cr:YAG, Cr.Forsterite, Yb:YAG, Yb:KGW, Yb:KYW, Yb:glass, KYbW and YbAG.

55. The method of claim 48, wherein the gain medium is Nd:YVO$_4$.

56. The method of claim 55, wherein the Nd:YVO$_4$ gain medium has a doping level of less than 0.5%.

57. The method of claim 48, wherein the diode pump source has an output wavelength of 880 nm.

58. The method of claim 48, wherein the harmonic conversion delivery device includes a second harmonic generator, a third harmonic generator and a delivery device.

* * * * *